(12) United States Patent
Feinberg

(10) Patent No.: US 9,038,198 B2
(45) Date of Patent: May 26, 2015

(54) AUTO DARKENING FILTER ADAPTER FRAME ASSEMBLY FOR A WELDING HELMET

(75) Inventor: Arnold Feinberg, Stoughton, MA (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 871 days.

(21) Appl. No.: 13/276,557

(22) Filed: Oct. 19, 2011

(65) Prior Publication Data

US 2013/0097760 A1    Apr. 25, 2013

(51) Int. Cl.
| A61F 9/06 | (2006.01) |
| G02B 7/00 | (2006.01) |
| G02B 7/02 | (2006.01) |
| G02B 5/23 | (2006.01) |

(52) U.S. Cl.
CPC .............. *G02B 7/006* (2013.01); *A61F 9/065* (2013.01); *G02B 7/02* (2013.01); *G02B 5/23* (2013.01)

(58) Field of Classification Search
CPC ................................ A61F 9/065; G02B 7/006
USPC .................................................. 2/8.1–8.4, 8.7
See application file for complete search history.

(56) References Cited

U.S. PATENT DOCUMENTS

| 5,533,206 | A | 7/1996 | Petrie et al. | |
|---|---|---|---|---|
| 5,857,215 | A | 1/1999 | Fergason et al. | |
| 6,151,711 | A | 11/2000 | Edwards | |
| 6,185,739 | B1 | 2/2001 | Verkic et al. | |
| 6,401,244 | B1 * | 6/2002 | Kramer et al. | 2/8.1 |
| 6,973,672 | B2 | 12/2005 | Huh | |
| 7,284,281 | B2 | 10/2007 | Huh | |
| 8,806,662 | B2 * | 8/2014 | Huh | 2/8.7 |
| 2008/0060102 | A1 | 3/2008 | Matthews et al. | |
| 2010/0287676 | A1 | 11/2010 | Seo | |

* cited by examiner

*Primary Examiner* — Anna Kinsaul
(74) *Attorney, Agent, or Firm* — Barlow, Josephs & Holmes, Ltd.

(57) ABSTRACT

An adapter frame assembly is provided to receive and support an extra-large 110 mm×110 mm ADF, safety lens and diopter within the viewing window of an existing welding helmet. The adapter frame assembly provides for replacement of the safety lens without removing the ADF and installation or removal of a diopter without removing the safety lens or diopter. The ADF, safety lens and diopter are all easy to install and change.

16 Claims, 12 Drawing Sheets

AUTO DARKENING FILTER ADAPTER FRAME ASSEMBLY FOR A WELDING HELMET

BACKGROUND

The present specification relates to welding helmets and more particularly, to an adapter frame assembly for mounting an extra-large auto darkening filter (ADF), safety lens and diopter within the viewing window of a welding helmet.

SUMMARY

An adapter frame assembly is provided to receive and support an extra-large 110 mm×110 mm ADF, safety lens and diopter within the viewing window of a welding helmet. The adapter frame assembly provides for replacement of the safety lens without removing the ADF, and installation and removal of a diopter without removing the safety lens or the ADF.

Generally, the welding helmet comprises a welding shield and a head gear for supporting the welding shield in front of the user's eyes. The welding shield includes a front wall and sidewalls extending outwardly and rearwardly. The front wall of the welding shield further includes an opening defined by knee walls extending rearwardly from the front wall and ledge walls extending inwardly from terminal edges of the knee walls. The knee and ledge walls form a seat into which the adapter frame is received. In turn, the adapter frame releasably receives and supports the ADF, the safety lens and the diopter within the opening.

The ADF and the safety lens are received and supported on a front side of the adapter frame assembly wherein the safety lens is removable without removing the ADF, and the diopter is received and supported on a rear side of the adapter frame where the diopter can be installed and removed without disturbing either the safety lens or the ADF.

More specifically, the adapter frame assembly comprises a frame body and a frame cover. The frame body has a front side, a rear side, and outer peripheral walls configured to be seated within the opening in the welding shield. The rear side of the frame body includes retention tabs which are releasably engaged with the ledge walls of the welding shield to releasably maintain the frame body in assembled relation with the welding shield. The front side of the frame body includes an inner seat configured to receive and support the ADF and further includes a retention mechanism configured to releasably retain the ADF in the inner seat. The front side of the frame body further includes an outer seat forward of the inner seat for receiving and supporting the safety lens in front of the ADF. The cover frame is releasably received in assembled relation with the frame body wherein the safety lens is captured in the outer seat between the frame body and the cover frame.

The rear side of the frame body includes a diopter seat configured to releasably receive and support the diopter behind said ADF, the diopter being removable from the frame body without removing the safety lens or the ADF.

Accordingly, an objective is to provide an adapter frame assembly which receives and supports an extra-large 110 mm×110 mm ADF, safety lens and diopter within the viewing window of an existing welding helmet It is another objective to provide for replacement of the safety lens without removing the ADF, and installation and removal of a diopter without removing the safety lens or the ADF.

Other objects, features and advantages shall become apparent as the description thereof proceeds when considered in connection with the accompanying illustrative drawings.

BRIEF DESCRIPTION OF THE DRAWING FIGURES

The preferred embodiment will now be described further by way of example with reference to the following examples and figures, which are intended to be illustrative only and in no way limiting upon the scope of the disclosure.

DETAILED DESCRIPTION OF THE PREFERRED EMBODIMENT

Figure 1:
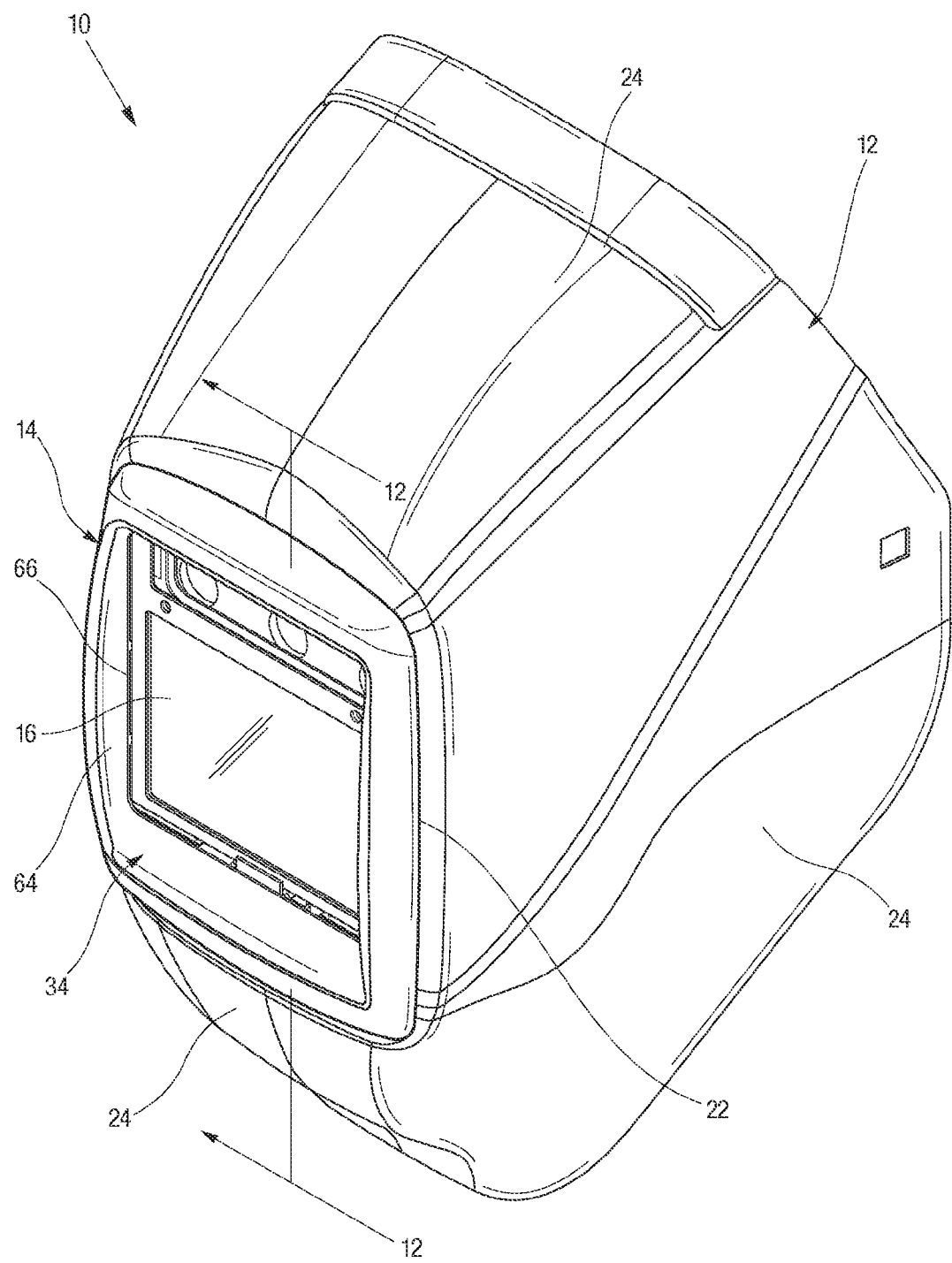
FIG. 1 is a perspective view of a welding helmet including the adapter frame assembly constructed in accordance with the teachings of the present disclosure.
Figure 2:
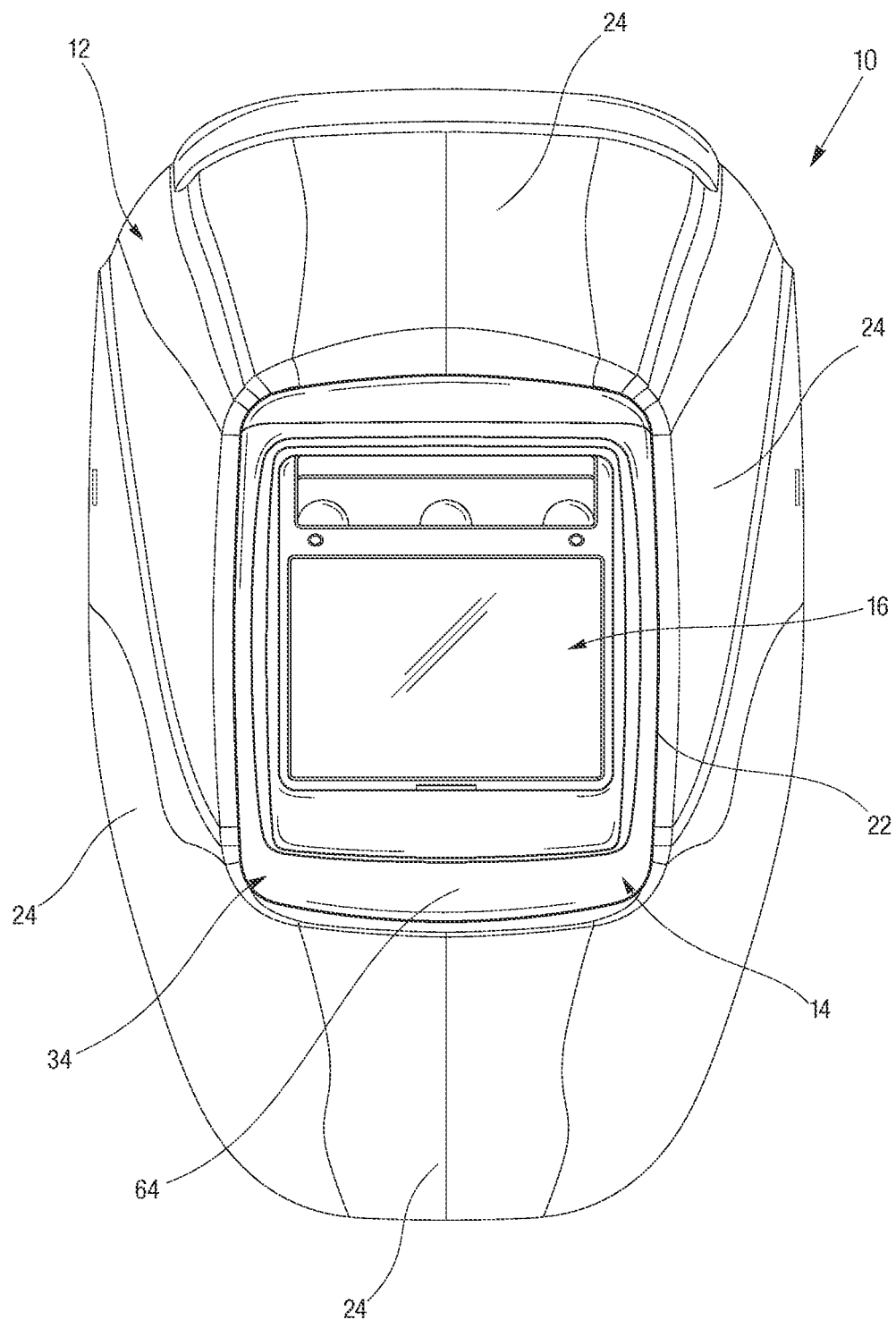
FIG. 2 is a front view thereof.
Figure 3:
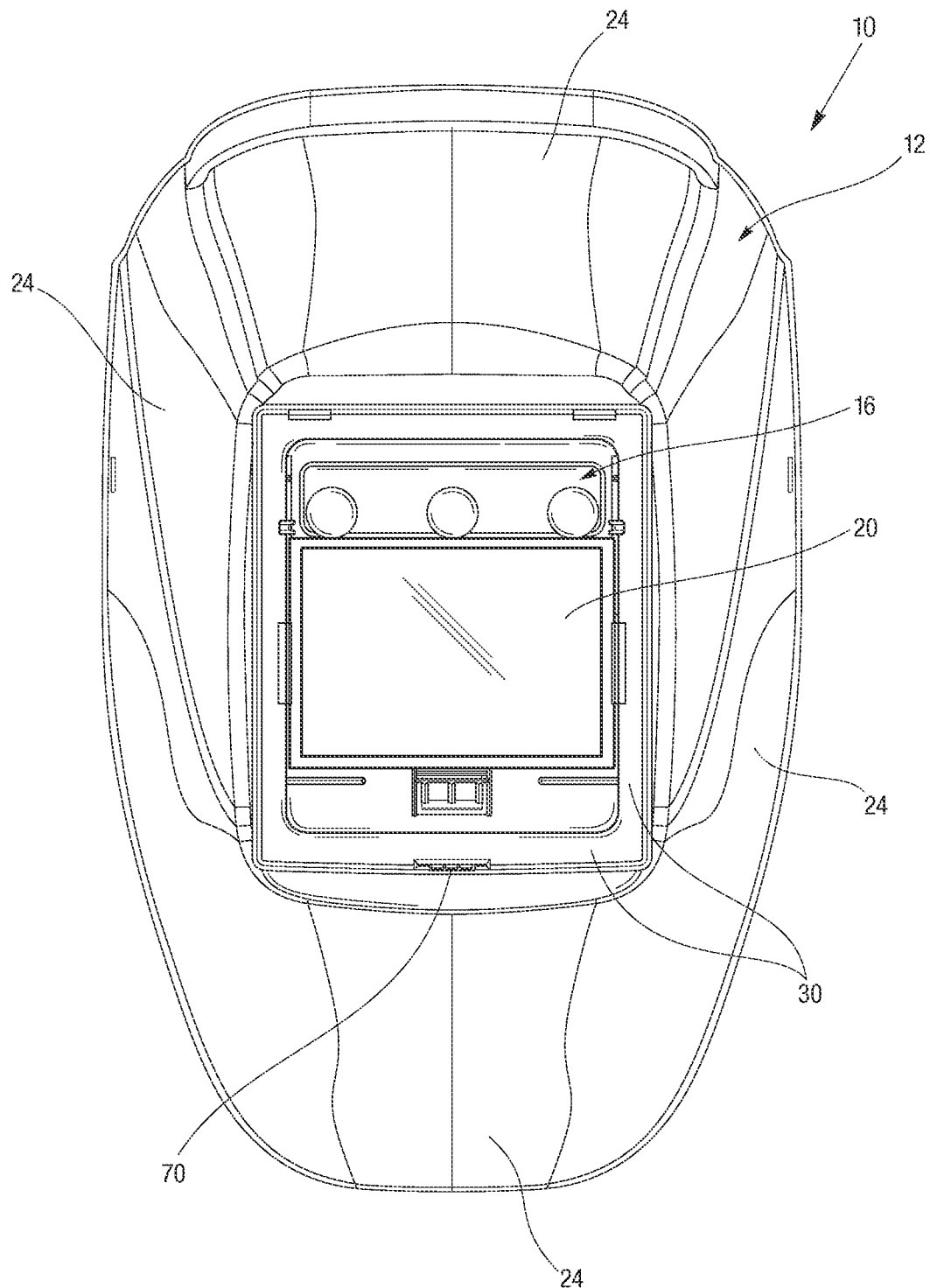
FIG. 3 is a rear view thereof.

A welding helmet assembly is generally indicated at 10 in FIGS. 1-4. The welding helmet assembly comprises a welding shield generally indicated at 12 and an adapter frame assembly generally indicated at 14, an auto darkening filter (ADF) 16, a safety lens 18, and a diopter 20. A helmet head gear (not shown) supports the welding shield 12 in front of the user's eyes. The ADF 16, safety lens 18 and diopter 20 are components which are known in the art and commercially available through various sources. In particular, the present disclosure is directed to an adapter frame assembly 14 which allows for the installation of an extra-large 110×110 mm ADF 16, which is considered to be desirable by those in the industry, into an existing welding helmet (Fibre Metal Model 2090) which was originally intended for use with a standard size ADF. (Fibre Metal is a trademark of Fibre Metal Products Company). While the present disclosure illustrates and describes the model 2090 welding helmet and an adapter frame configured for that model, the teachings and concepts disclosed herein are not limited to any particular welding helmet.

The adapter frame 14 receives and supports the ADF 16, the safety lens 18 and the diopter 20 within a viewing window of the welding shield 12. The adapter frame assembly 14 provides for replacement of the safety lens 18 without removing the ADF 16, and installation and removal of the diopter 20 without removing the safety lens 18 or the ADF 16.

Generally, the welding shield 12 includes a front wall 22 and a plurality of side walls 24 extending outwardly and rearwardly from the front wall 22 to form a concave enclosure for the user's face and head. The front wall 22 of the welding shield 12 includes an opening 26, or viewing window, defined on its peripheral edges by knee walls 28 extending rearwardly from the front wall 22 and ledge walls 30 extending inwardly from terminal edges of the knee walls 28. The knee walls 28 and ledge walls 30 form a seat into which the adapter frame assembly 14 is received. In turn, the adapter frame assembly 14 releasably receives and supports the ADF 16, the safety lens 18 and the diopter 20 within the opening 26.

Figure 4:
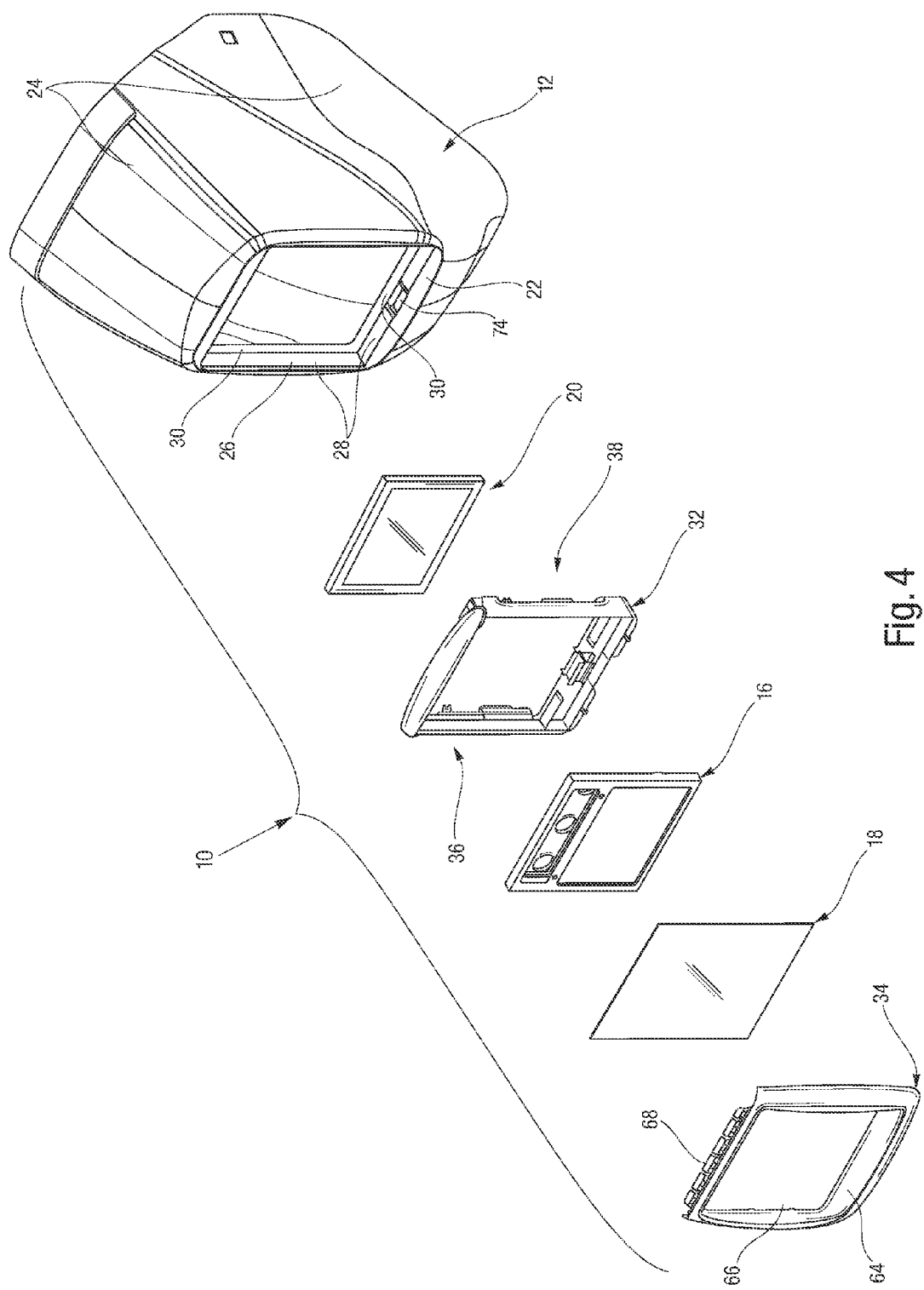
FIG. 4 is an exploded perspective view thereof.

Referring to FIG. 4, the ADF 16 and the safety lens 18 are received and supported on a front side of the adapter frame assembly 14 wherein the safety lens 18 is removable without removing the ADF 16, and the diopter 20 is received and supported on a rear side of the adapter frame assembly 14 (accessible from inside the welding shield 12) where the diopter 20 can be installed and removed without disturbing either the safety lens 18 or the ADF 16.

Referring to FIGS. 4-12, the adapter frame assembly 14 comprises a frame body generally indicated at 32 and a frame cover generally indicated at 34. The frame body 32 and frame cover 34 are molded from a plastic material having at least some level of elastomeric flexibility which allows flexible tabs and latches to be integrally formed therewith.

The frame body 32 has a front side 36, a rear side 38, and outer peripheral walls 40 configured to be seated in snug interfitting relation within the opening 26 in the welding shield 12. The rear side 38 of the frame body 32 includes opposing retention tabs 42 which are releasably engaged with the ledge walls 30 of the welding shield 12 to releasably maintain the frame body 32 in assembled relation with the welding shield 12.

Figure 5:
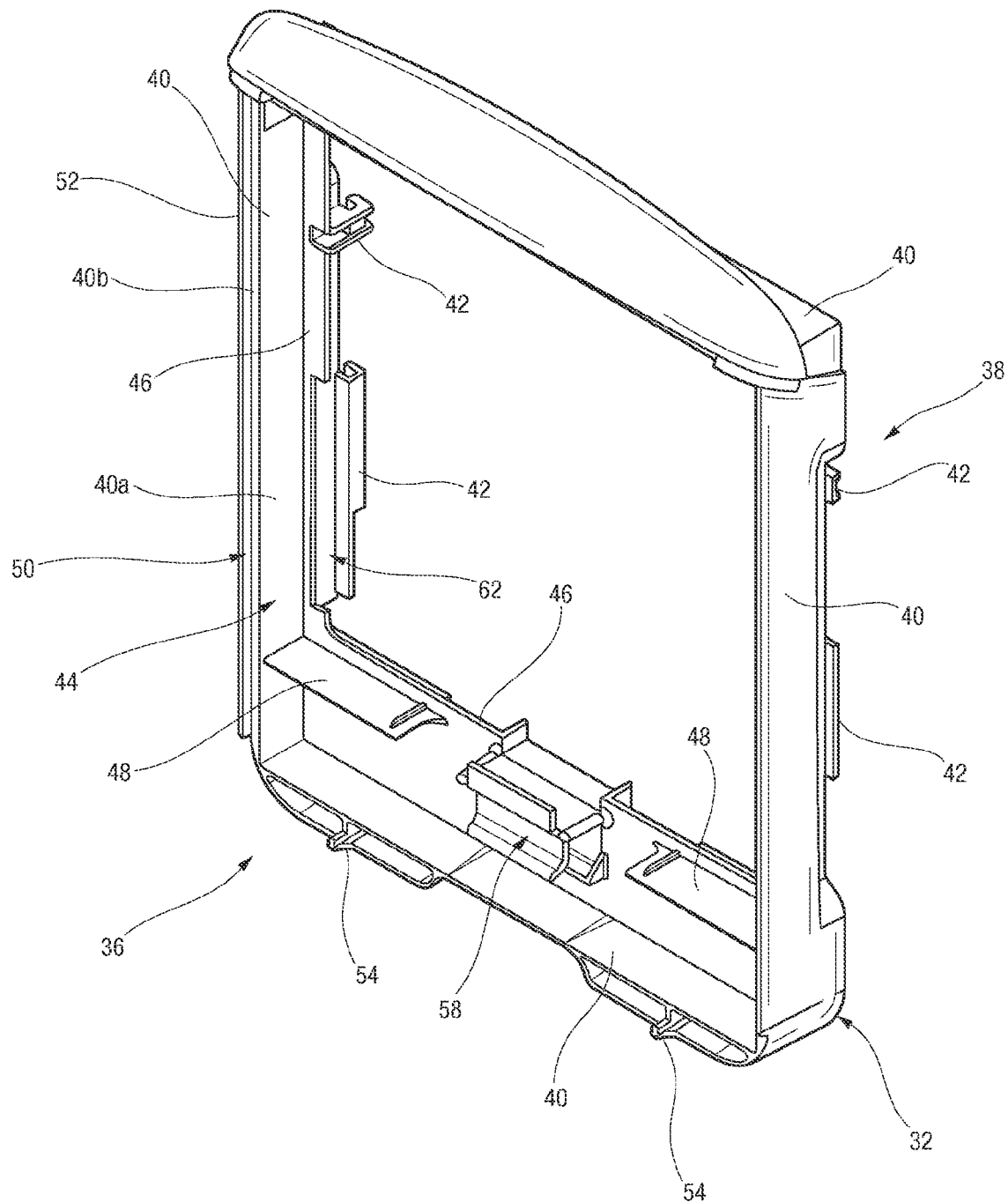
FIG. 5 is a front perspective view of the frame body of the adapter frame assembly looking from the upper right.

The front side 36 of the frame body 32 includes an inner seat configured to receive and support the ADF 16 and further includes a retention mechanism configured to releasably retain the ADF 16 in the inner seat. Referring to FIG. 5, the inner seat is defined on the top and sides by the inner surfaces 40a of the outer peripheral walls 40, in the back by a shoulder wall 46 extending inwardly from the inner surfaces 40a and on the bottom by a pair of spaced shelves 48 projecting forwardly from the shoulder wall 46.

The front side 36 of the frame body 32 further includes an outer seat 50 forward of the inner seat 44 for receiving and supporting the safety lens 18 in front of the ADF 16. The outer seat 50 is defined in the back by a narrow front surface 40b of the peripheral side walls 40, on the top and sides by a ridge wall 52 extending forwardly from the front surface 40b of the side walls 40, and on the bottom by spaced finger tabs 54.

Figure 6:
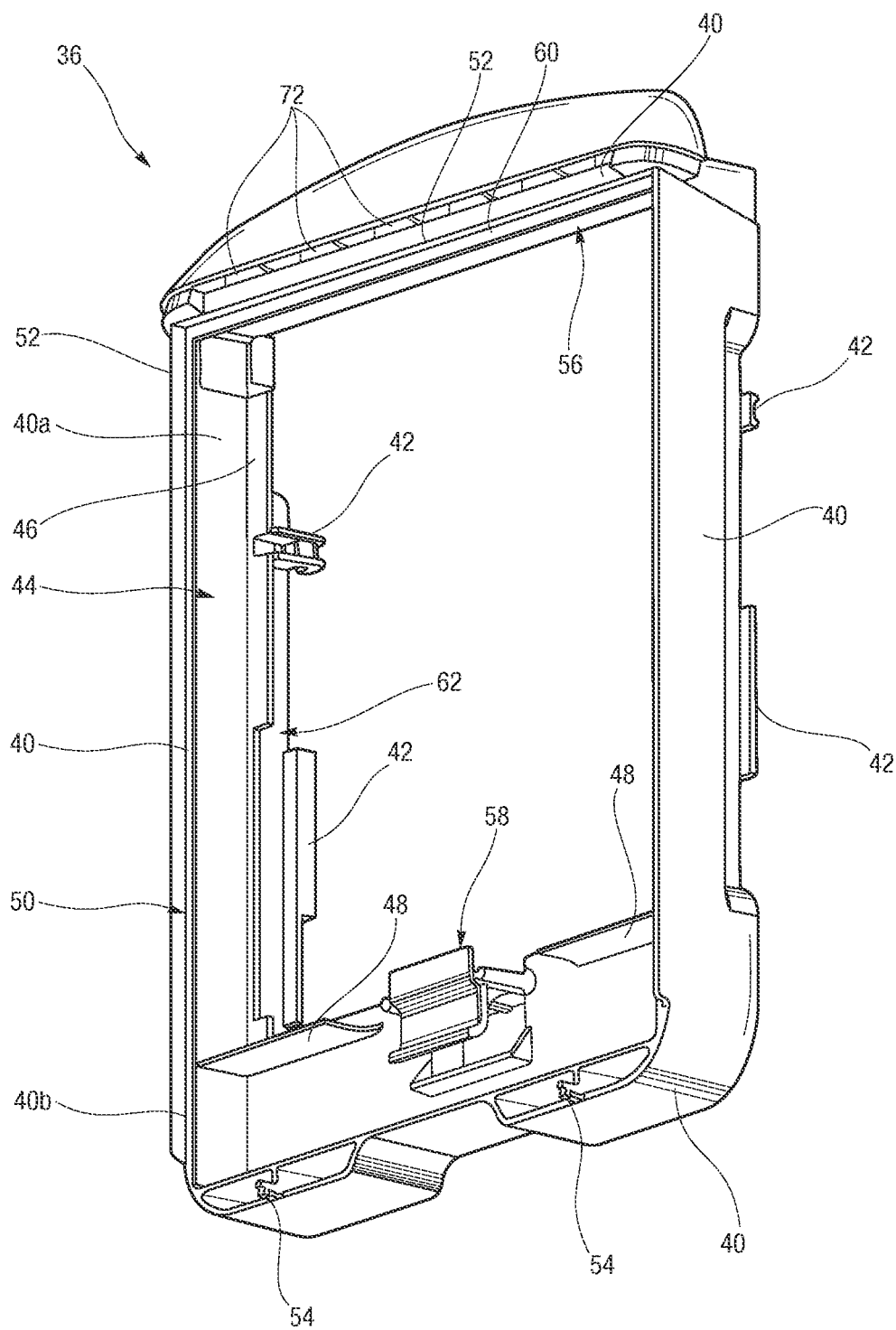
FIG. 6 is another front perspective view thereof looking from the lower right.

Still referring to FIG. 6, the ADF retention mechanism comprises a notch 56 in an upper portion of the inner seat 44 for receiving an upper edge of the ADF 16, and a flexible latch hook 58 on a lower portion of the seat 44 opposite the notch 56. The notch 56 is formed by the upper portion of the shoulder wall 46 and a downwardly extending ridge wall 60 spaced forwardly from the shoulder wall 46.

The ADF 16 is seated in the inner seat 44 with the upper edge thereof captured in the notch 56 and the lower edge captured by the flexible latch hook 58. The safety lens 18 is received in the outer seat 50 in front of the ADF 16, in snug interfitting relation (friction fit).

Figure 7:
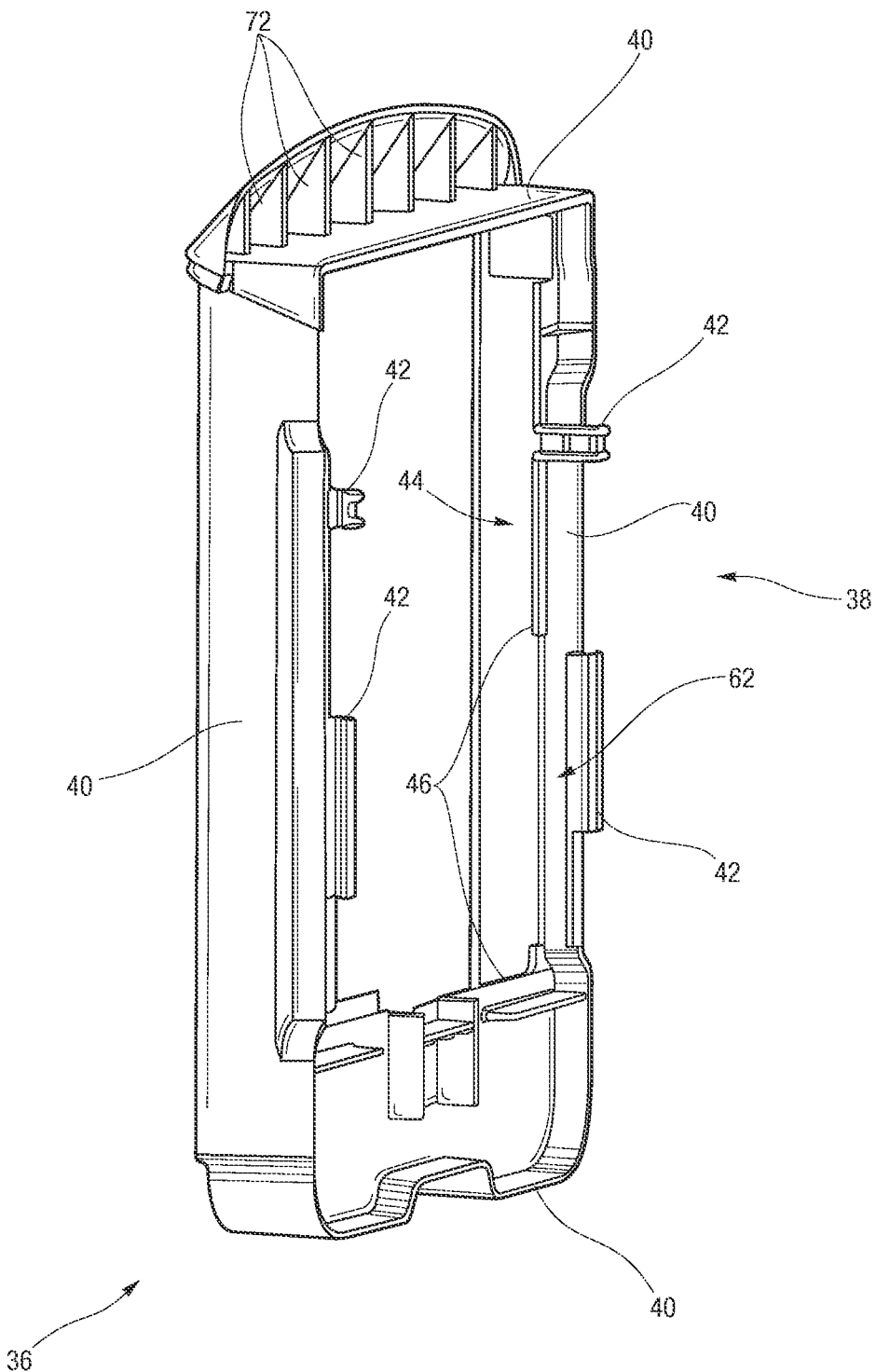
FIG. 7 is a rear perspective view thereof looking from the lower right.
Figure 8:
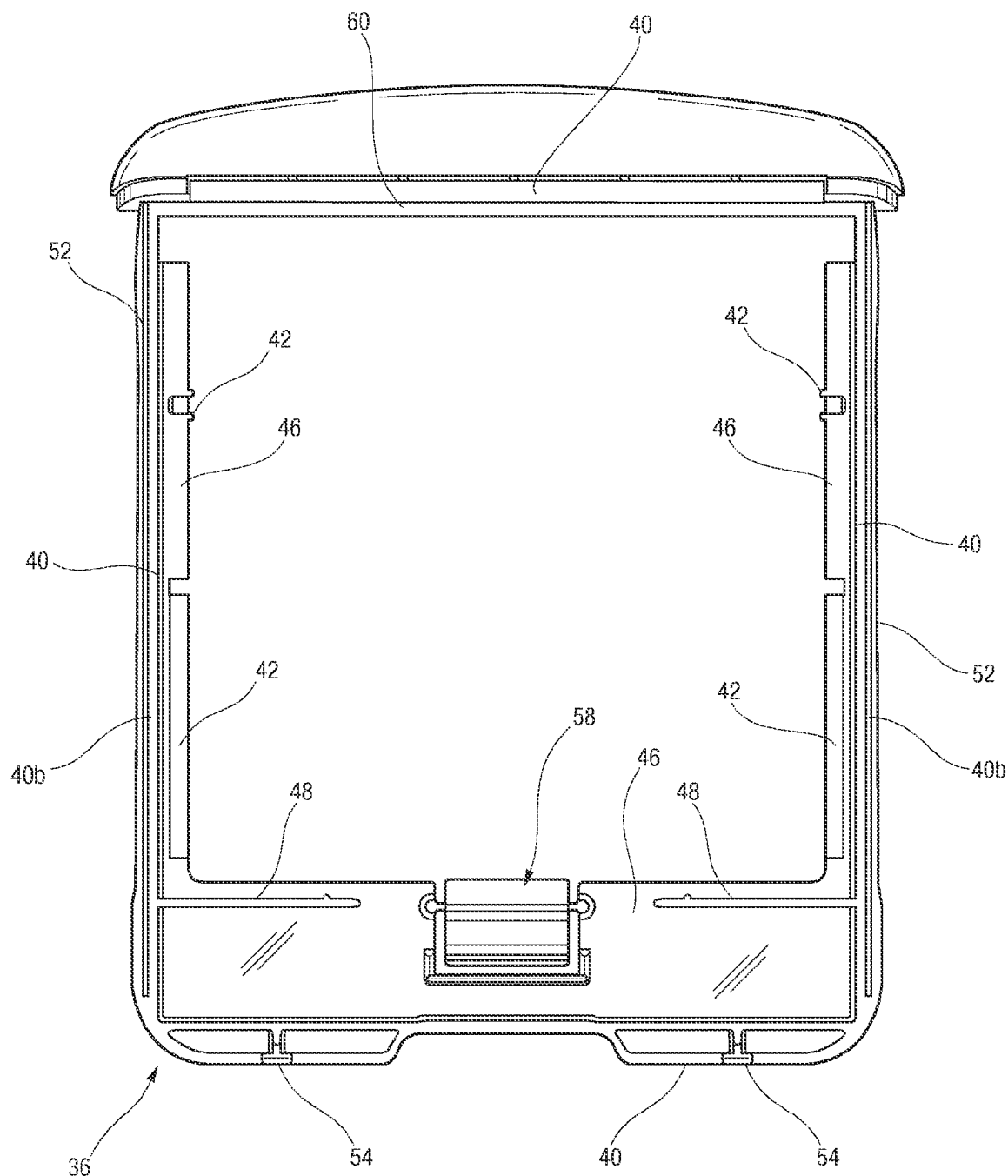
FIG. 8 is a front view thereof.
Figure 9:
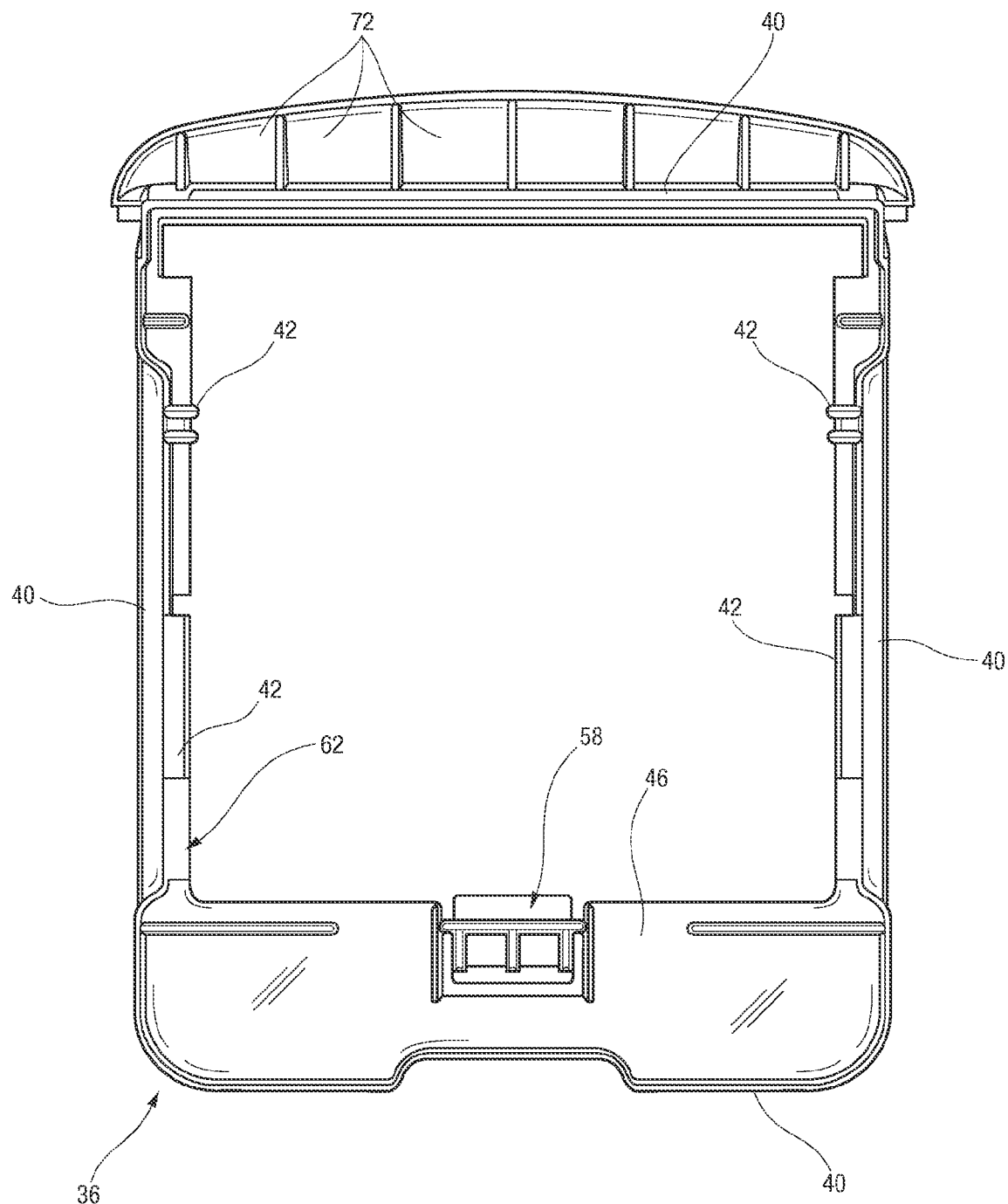
FIG. 9 is a rear view thereof.

Referring to FIG. 7, the rear side 38 of the frame body 32 includes a diopter seat 62 configured to releasably receive and support the diopter 20 behind the ADF 16, the diopter 20 being removable from the frame body 32 without removing the safety lens 18 or the ADF 16. The diopter seat 62 is defined in the front by the rear surface of the shoulder wall 46, on the sides by the inner surfaces 40a of the outer peripheral walls 40, and in the back by the rear surfaces of the retention tabs 42. The diopter 20 can be slid into and out of the diopter seat 20 from the rear (inside the welding helmet) without removing the safety lens 18 or the ADF 16.

Figure 10:
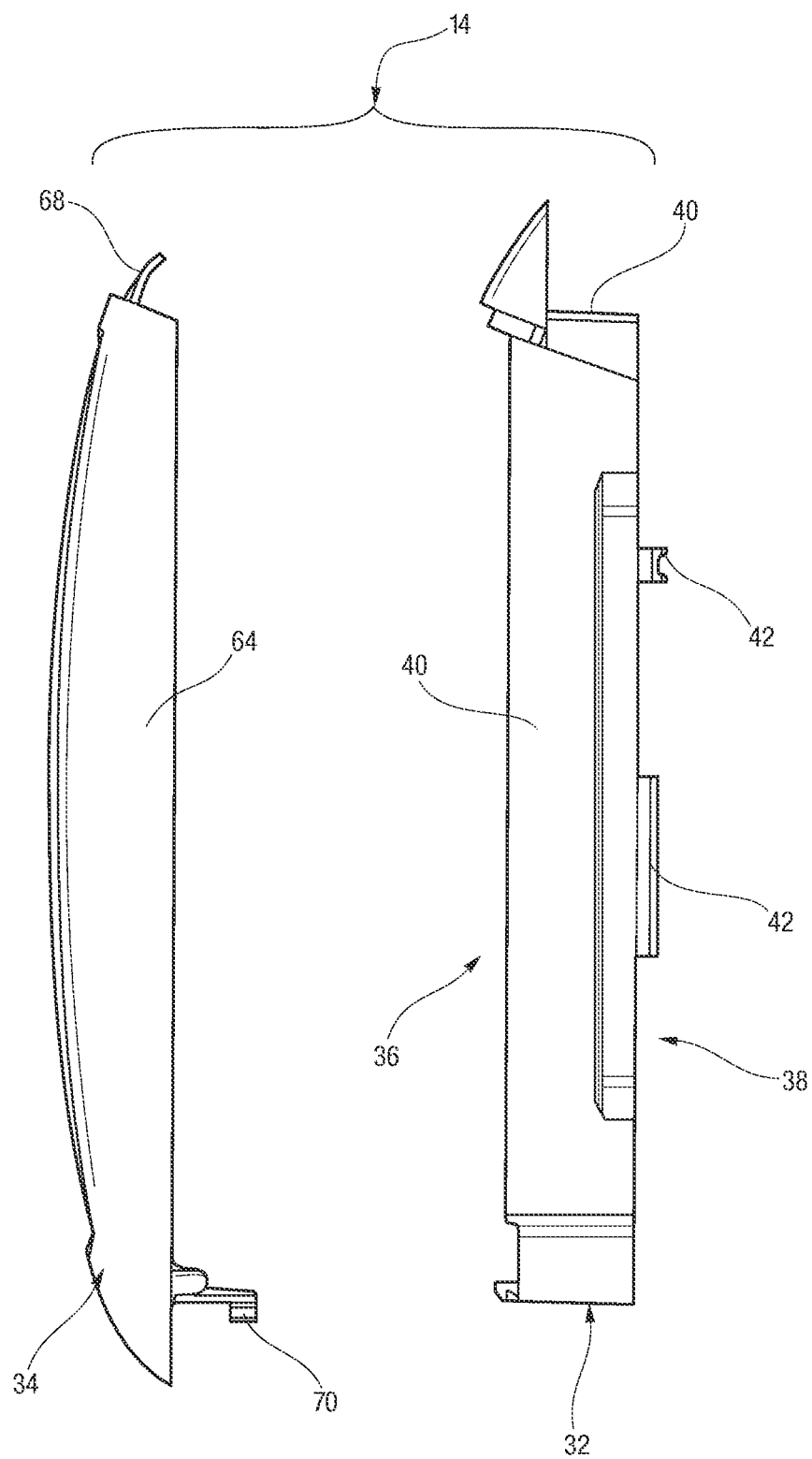
FIG. 10 is an exploded side view of the adapter frame assembly showing the frame body and frame cover.
Figure 11:
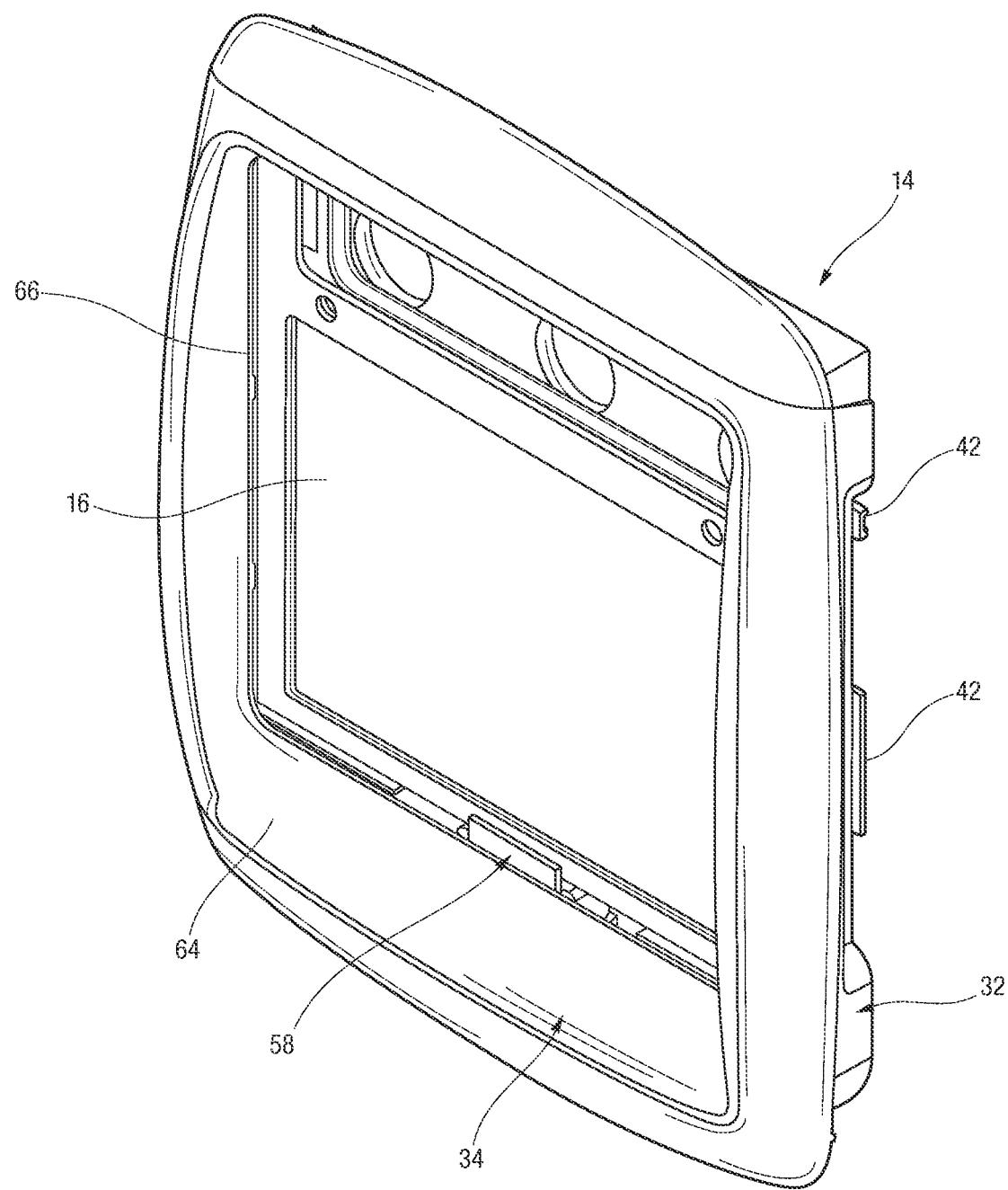
FIG. 11 is a perspective view of the adapter frame assembly including the ADF, safety lens and diopter installed therein.
Figure 12:
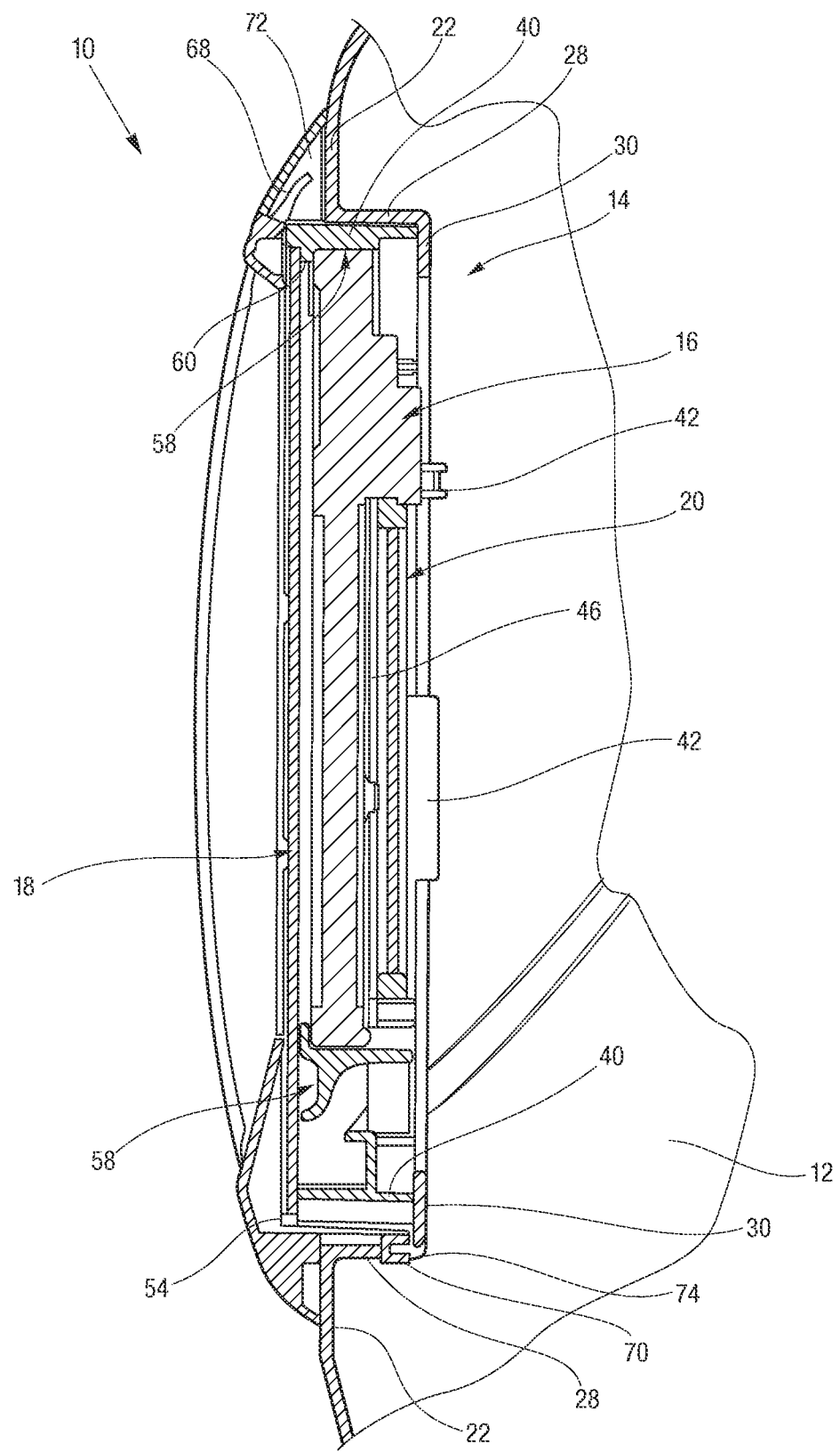
FIG. 12 is a cross-sectional view thereof taken along line 12-12 of FIG. 1.

Referring to FIGS. 10-12, the cover frame 34 is releasably received in assembled relation with the frame body 32 wherein the safety lens 18 is captured in the outer seat 50 between the frame body 32 and the cover frame 34. The cover frame 34 comprises peripheral outer walls 64 defining a viewing window 66, tabs 68 on an upper portion thereof and a flexible locking tab 70 on a lower portion thereof opposite the tabs 68. The tabs 68 are received in interfitting relation with mating notches 72 in upper portion of the frame body 32, and the flexible locking tab 70 is releasably engaged in a mating notch 74 in the lower knee wall 28 of the opening 26 in the shield 12 for releasably maintaining the cover frame 34 in assembled relation with the frame body 32.

In an exemplary assembly, the frame body 32 is mounted within the welding shield 12 opening by snapping the retention tabs 42 into engagement with the ledge walls 30. This creates a new adapter arrangement for mounting of the ADF 16, safety lens 18 and diopter 20. The ADF 16 is then mounted in the inner seat 44 by tilting and sliding the upper edge into the notch 56 in the top of the inner seat 44 and then rotating the lower edge of the ADF 16 into engagement with the flexible latch hook 58. The safety lens 18 is then seated in front of the ADF 16 in a snug friction fit within the outer seat 50. Finally, the cover frame 34 is assembled by inserting the tabs 68 into the mating notches 72 in the upper portion of the frame body 32 and rotating the lower edge downwardly so that the flexible locking tab 70 slides under the lower edge of the frame body 32 and into the mating notch 74 in the lower knee wall 28. In this regard, the inner surfaces of the cover frame 34 engage the front surface of the safety lens 18 and snugly capture the safety lens 18 between the rear of the cover frame 34 and the outer seat 50. It can be appreciated that the safety lens 18 can be removed and changed without removing the ADF 16 by simply removing the cover frame 34 and swapping out the old safety lens 18 for a new safety lens 18.

The diopter 20 can be slid into and out of the diopter seat 62 from the inside of the shield 12 at any time before or after assembly of the ADF 16 and safety lens 18. It can thus be seen that providing the diopter seat 62 on the rear of the frame body 32 allows the diopter 20 to be installed and removed without disturbing the safety lens 18 or the ADF 16.

For these reasons, the adapter frame as described herein is believed to represent a significant advancement in the art, which has substantial commercial merit.

While there is shown and described herein certain specific structure embodying the adapter frame assembly, it will be manifest to those skilled in the art that various modifications and rearrangements of the parts may be made without departing from the spirit and scope of the underlying concept and that the same is not limited to the particular forms herein shown and described except insofar as indicated by the scope of the appended claim.

What is claimed is:

1. A welding helmet comprising:
a welding shield including a front wall and a plurality of side walls extending outwardly and rearwardly therefrom, said welding shield further including an opening in said front wall, said opening being defined by knee walls extending rearwardly from said front wall and ledge walls extending inwardly from terminal edges of said knee walls; and
an adapter frame assembly releasably secured within said opening, said adapter frame assembly includes a frame body having a front side and a rear side defined by a shoulder wall, the frame body configured to receive and support an auto darkening filter (ADF), a safety lens and a diopter within said opening,
wherein said ADF and said safety lens are received and supported on said front side of said adapter frame body and said safety lens is removable without removing said ADF, and further wherein said diopter is received and supported on said rear side of said adapter frame body.

2. A welding helmet comprising:
a welding shield including a front wall and a plurality of sidewalls extending outwardly and rearwardly therefrom, said welding shield further including an opening in said front wall, said opening being defined by knee walls extending rearwardly from said front wall and ledge walls extending inwardly from terminal edges of said knee walls; and
an adapter frame assembly releasably secured within said opening, said adapter frame being configured to releasably receive and support an auto darkening filter (ADF) and a safety lens within said opening,
said adapter frame assembly comprising a frame body having a front side and rear side defined by a shoulder wall and outer peripheral walls configured to be seated within said opening,
retention tabs on said frame body releasably engaged with said ledge walls to releasably maintain said frame body in assembled relation with said welding shield;
said front side of said frame body including an inner seat configured to receive and support said ADF, said front side of said frame body further including a retention mechanism configured to releasably secure said ADF in assembled relation with said frame body within said inner seat; and
a cover frame releasably received in assembled relation with said frame body.

3. The welding helmet of claim 2 wherein said front side of said frame body further includes an outer seat forward of said inner seat for receiving and supporting said safety lens in front of said ADF, said safety lens being captured in said outer seat between said frame body and said cover frame.

4. The welding helmet of claim 2 wherein said retention mechanism comprises a notch in a first portion of said inner seat for receiving an edge of said ADF, and a flexible latch on a second portion of said inner seat opposite said notch.

5. The welding helmet of claim 3 wherein said retention mechanism comprises a notch in a first portion of said inner seat for receiving an edge of said ADF, and a flexible latch on a second portion of said inner seat opposite said notch.

6. The welding helmet of claim 2 wherein said cover frame comprises tabs on a first portion thereof and a flexible locking tab on a second portion thereof opposite said tabs, said tabs being received in interfitting relation with mating notches in said frame body, said flexible locking tab engaging with a mating notch in said knee walls of said opening in said shield for releasably maintaining said cover frame in assembled relation with said frame body.

7. The welding helmet of claim 3 wherein said cover frame comprises tabs on a first portion thereof and a flexible locking tab on a second portion thereof opposite said tabs, said tabs being received in interfitting relation with mating notches in said frame body, said flexible locking tab engaging with a mating notch in said knee walls of said opening in said shield for releasably maintaining said cover frame in assembled relation with said frame body.

8. The welding helmet of claim 5 wherein said cover frame comprises tabs on a first portion thereof and a flexible locking tab on a second portion thereof opposite said tabs, said tabs being received in interfitting relation with mating notches in said frame body, said flexible locking tab engaging with a mating notch in said knee walls of said opening in said shield for releasably maintaining said cover frame in assembled relation with said frame body.

9. A welding helmet comprising:
a welding shield including a front wall and a plurality of sidewalls extending outwardly and rearwardly therefrom, said welding shield further including an opening in said front wall, said opening being defined by knee walls extending rearwardly from said front wall and ledge walls extending inwardly from terminal edges of said knee walls; and
an adapter frame assembly releasably secured within said opening, said adapter frame assembly comprising a front side and rear side defined by a shoulder wall, said adapter frame assembly being configured to releasably receive and support an auto darkening filter (ADF), a diopter and a safety lens within said opening,
wherein said ADF and said safety lens are received and supported on said front side of said adapter frame assembly and said safety lens is removable without removing said ADF, and further wherein said diopter is received and supported on said rear side of said adapter frame assembly,
wherein said rear side of said adapter frame assembly includes a diopter seat configured to releasably receive and support said diopter behind said ADF, said diopter being removable from said adapter frame assembly without removing said ADF.

10. An adapter frame assembly for receiving and supporting an auto darkening filter (ADF) within an opening of a welding helmet, said adapter frame assembly comprising:
a frame body having a front side and a rear side defined by a shoulder wall and outer peripheral walls configured to be seated within said opening of said welding helmet;
the opening of said welding helmet in a front wall with a plurality of sidewalls extending outwardly and rearwardly therefrom, the opening further defined by knee walls extending rearwardly from said front wall and ledge walls extending inwardly from terminal edges of said knee walls; and
retention tabs on said frame body releasably engaged with said ledge walls to releasably maintain said frame body in assembled relation with said welding helmet, said front side of said frame body including an inner seat configured to receive and support said ADF,
said front side of said frame body including an inner seat configured to receive and support said ADF, said front side of said frame body further including a retention mechanism configured to releasably secure said ADF in assembled relation with said frame body within said inner seat; and
a cover frame releasably received in assembled relation with said frame body.

11. The adapter frame assembly of claim 10 wherein said front side of said frame body further includes an outer seat forward of said inner seat for receiving and supporting a safety lens in front of said ADF, said safety lens being captured in said outer seat between said frame body and said cover frame.

12. The adapter frame assembly of claim 10 wherein said retention mechanism comprises a notch in a first portion of said inner seat for receiving an edge of said ADF, and a flexible latch on a second portion of said inner seat opposite said notch.

13. The adapter frame assembly of claim 11 wherein said retention mechanism comprises a notch in a first portion of said inner seat for receiving an edge of said ADF, and a flexible latch on a second portion of said inner seat opposite said notch.

14. The adapter frame assembly of claim 10 wherein said cover frame comprises tabs on a first portion thereof and a flexible locking tab on a second portion thereof opposite said tabs, said tabs being received in interfitting relation with mating notches in said frame body, said flexible locking tab engaging with a mating notch in said knee walls of said opening in said welding helmet for releasably maintaining said cover frame in assembled relation with said frame body.

15. The adapter frame assembly of claim 11 wherein said cover frame comprises tabs on a first portion thereof and a flexible locking tab on a second portion thereof opposite said tabs, said tabs being received in interfitting relation with mating notches in said frame body, said flexible locking tab engaging with a mating notch in said knee walls of said opening in said welding helmet for releasably maintaining said cover frame in assembled relation with said frame body.

16. The adapter frame assembly of claim 10 wherein said rear side of said frame body includes a diopter seat configured to releasably receive and support said diopter behind said ADF, said diopter being removable from said frame body without removing said ADF.

* * * * *